(12) United States Patent
Kim et al.

(10) Patent No.: US 8,742,160 B2
(45) Date of Patent: Jun. 3, 2014

(54) METHOD FOR PREPARING TRICYCLIC DERIVATIVES

(75) Inventors: Myung-Hwa Kim, Yongin-si (KR); In-Hae Ye, Yongin-si (KR); Jong-Hee Choi, Suwon-si (KR)

(73) Assignee: JE IL Pharmaceutical Co., Ltd., Seoul (KR)

( * ) Notice: Subject to any disclaimer, the term of this patent is extended or adjusted under 35 U.S.C. 154(b) by 143 days.

(21) Appl. No.: 13/381,036

(22) PCT Filed: Jun. 29, 2010

(86) PCT No.: PCT/KR2010/004212
§ 371 (c)(1),
(2), (4) Date: Dec. 27, 2011

(87) PCT Pub. No.: WO2011/004980
PCT Pub. Date: Jan. 13, 2011

(65) Prior Publication Data
US 2012/0101296 A1    Apr. 26, 2012

(30) Foreign Application Priority Data
Jul. 8, 2009    (KR) .................. 10-2009-0061983

(51) Int. Cl.
*C07C 321/28*    (2006.01)
*C07C 323/42*    (2006.01)

(52) U.S. Cl.
USPC ............................. 560/103; 560/19

(58) Field of Classification Search
USPC ................................. 560/19, 103
See application file for complete search history.

(56) References Cited

U.S. PATENT DOCUMENTS

2007/0179143 A1    8/2007    Kim et al.

FOREIGN PATENT DOCUMENTS

| KR | 10-2005-0001383 | | 1/2005 | |
|----|-----------------|---|--------|---|
| WO | 02-100824 A1 | | 12/2002 | |
| WO | WO-02/100824 A1 | * | 12/2002 | ............ C07C 323/41 |
| WO | 2004-113281 A1 | | 12/2004 | |

OTHER PUBLICATIONS

Guan, J., et al., "Antitumor Agents. 185. Synthesis and Biological Evaluation of Tridemethylthiocolchicine Analogues as Novel Topoisomerase II Inhibitors", Journal of Medicinal Chemistry, 1998, 41 (11), pp. 1956-1961, ISSN: 0022-2623.

Marzi, E., et al., "Fluoro-or trifluoromethyl-substinued benzyl and phenethyJ alcohols: Substrates for metal-mediated site-selective functionalization", European Journal of Organic Chemistry, 2002, (15), pp. 2508-2517, ISSN: 1434-193X.

* cited by examiner

*Primary Examiner* — Kamal Saeed
*Assistant Examiner* — Janet L Coppins
(74) *Attorney, Agent, or Firm* — Lucas & Mercanti, LLP

(57) ABSTRACT

The present invention relates to a method for preparing a tricyclic derivative, and more particularly, to a method for preparing a tricyclic derivative intermediate with high yield and purity, the method including: introducing a hydroxy group by esterifying and substituting 2-fluoroisophtalic acid compound; introducing a piperidyl group; introducing a hydroxy group through reduction reaction; and then hydrolyzing the resultant compound, and to a method for preparing the tricyclic derivative using said intermediate. According to the method of the present invention, it is possible to provide a tricyclic derivative and an intermediate thereof with high productivity and economic feasibility as well as high purity and yield, by purifying a compound using re-crystallization unlike typical methods of using column chromatography. In addition, the method of the present invention can be usefully used for industrial mass production because sodium borohydride or lithium aluminum hydride with low risk of a fire is used unlike typical methods of using lithium borohydride which is not industrially applicable due to high risk of a fire.

20 Claims, No Drawings

METHOD FOR PREPARING TRICYCLIC DERIVATIVES

CROSS-REFERENCE TO RELATED APPLICATIONS

This application is a 371 of PCT/KR2010/004212, filed Jun. 29, 2010, which claims the benefit of Korean Patent Application No. 10-2009-0061983, filed Jul. 8, 2009, the contents of each of which are incorporated herein by reference.

TECHNICAL FIELD

The present invention relates to a method for preparing an intermediate of a tricyclic derivative with high purity and high yield, and a method for preparing a tricyclic derivative using the intermediate.

BACKGROUND ART

It is known that a tricyclic derivative has very strong cytotoxicity to a cancer cell line; significantly decreases a toxicity rather than colchicine or taxol injections in an animal toxicity test; significantly decreases a size and weight of tumor; and strongly suppresses an angiogenesis in HUVEC cell so that it can be used as an anticancer drug, an antiproliferative, and an angiogenesis inhibitor usefully.

Korean Patent Registration No. 0667464 discloses a method for synthesizing a compound represented by the following Chemical Formula 2 that is an important intermediate for synthesizing a tricyclic derivative compound represented by the following Chemical Formula 1:

[Chemical Formula 1]

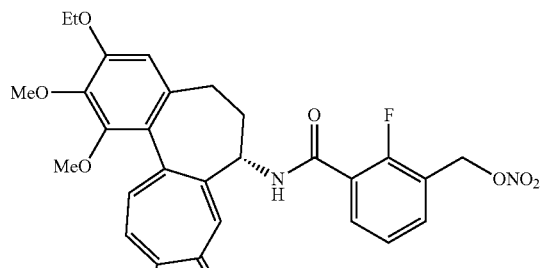

[Chemical Formula 2]

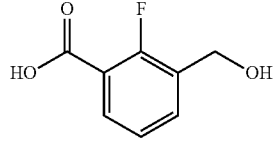

As shown in the following Reaction Formula 4, the intermediate compound of Chemical Formula 2 is synthesized through hydrolysis, after synthesizing a compound of Chemical Formula 6, through esterification of a compound of Chemical Formula 5 and methanol, and synthesizing a compound of Chemical Formula 11 with one ester group reduced through a reduction reaction using lithium borohydride ($LiBH_4$) as a reducing agent:

[Reaction Formula 4]

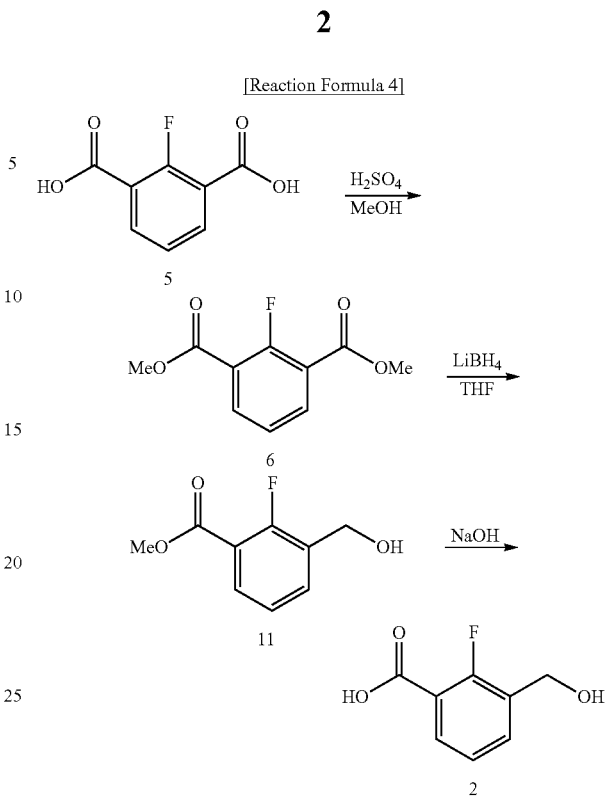

However, the preparing method of Reaction Formula 4 is not suitable to be applied to industrial production because this method uses lithium borohydride ($LiBH_4$) as a reducing agent, which violently reacts with water to cause harmful gas and flammable gas to be generated, and also has a risk of ignition. Additionally, in the case of using sodium borohydride ($NaBH_4$) or lithium aluminum hydride ($LiAlH_4$) that are more easily handled as a reducing agent, there is a limitation that selectivity is decreased to thereby reduce all of two ester groups of the compound of Chemical Formula 6. Furthermore, the preparing method of Reaction Formula 4 has limitations that the compound of Chemical Formula 11 is purified using column chromatography and its yield is also very low as 58%, and when the compound of Chemical Formula 11 is purified with a re-crystallization, impurities are not completely removed and the tricyclic derivative compound of Chemical Formula 1 that is a final target compound has low purity.

Also, [European Journal of Organic Chemistry, 15, 2508 (2002)] discloses a method for synthesizing an intermediate compound of Chemical Formula 2 through deprotection reaction, after preparing a solution by adding, at −78° C., sec-butyllithium and N,N,N',N'',N''-pentamethyldiethylenetriamine to 2-fluorobenzylalcohol of Chemical Formula 13 with a hydroxy group protected and then synthesizing an intermediate of Chemical Formula 14 by adding the solution to carbon dioxide in a solid phase, as shown in the following Reaction Formula 5:

[Reaction Formula 5]

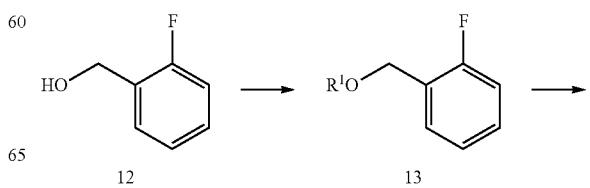

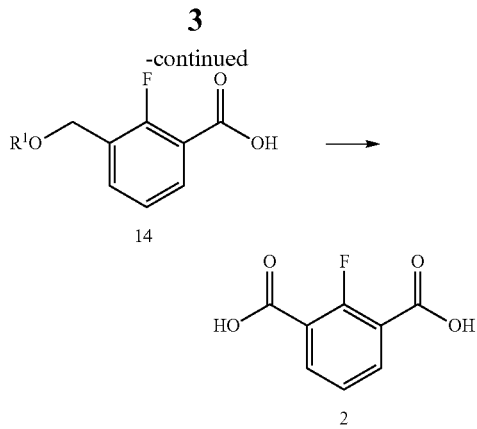

(where, $R^1$ is methoxymethyl group or triisopropylsilyl group).

However, the preparing method of Reaction Formula 5 is not preferable in an industrial aspect because when the hydroxyl group in Chemical Formula 12 is protected with methoxymethyl group, the yield is very low as 36% and when the hydroxyl group is protected with triisopropylsilyl group, the yield is increased as 61%, but boron trifluoride diethyl etherate with strong toxicity and corrosiveness, and high risk of a fire should be used for the deprotection reaction. Furthermore, a process using sec-butyllithium with the risk of ignition is not suitable to be applied to industrial production. Also, there is no knowing as to whether a process for maintaining a reaction temperature of −78° C. to proceed a reaction and a process for dropping a solution of −75° C. to carbon dioxide in a solid phase are industrially applicable or not.

The process for preparing the tricyclic derivative compound of Chemical Formula 1 from the intermediate compound of Chemical Formula 2 is disclosed in the existing patent (Korean Patent Registration No. 0667464). However, this conventional method provides a column chromatography method as a method for purifying the intermediate compound of Chemical Formula 2, the intermediates obtained in each step, and the tricyclic derivative compound of Chemical Formula 1 that is a final product. According to this method, when the purification amount is small, the compound with high purity can be obtained; however, a large quantity of the compound cannot be purified and thus the column chromatography is not industrially suitable. Moreover, the column chromatography uses an excess amount of expensive silica gel to cause an additional industrial waste to be produced, and therefore it is uneconomical.

Therefore, while the present inventors has been conducting a study on a method for preparing the tricyclic derivative of Chemical Formula 1 in order to solve the problems of the conventional techniques, the present inventors found a high-yielding preparation method for synthesizing and purifying the compound of Chemical formula 1 with high purity from the intermediate compound of Chemical Formula 2 which was synthesized by using an intermediate prepared with a new method, and finally the inventors have completed the present invention.

DISCLOSURE

Technical Problem

One object of the present invention is to provide a method for preparing a new tricyclic derivative with high productivity and economic feasibility.

Another object of the present invention is to provide a method for preparing a compound of Chemical Formula 2 with high yield and purity.

Another object of the present invention is to provide an intermediate compound produced during a process for preparing the compound of Chemical Formula 2 with high yield and purity.

Technical Solution

In order to achieve the above objects, the present invention provides a method for preparing a tricyclic derivative with high productivity and economic feasibility.

Furthermore, the present invention provides a method for preparing a compound of Chemical Formula 2 with high yield and purity, the method including: introducing a hydroxy group by esterifying and substituting 2-fluoroisophthalic acid compound; introducing a piperidyl group; introducing a hydroxy group through reduction reaction; and then hydrolyzing the resultant compound.

Furthermore, the present invention provides an intermediate compound which is produced during a process for preparing the compound of Chemical Formula 2.

Advantageous Effects

According to the method of the present invention, it is possible to provide a tricyclic derivative and an intermediate thereof with high productivity and economic feasibility as well as high purity and yield by purifying a compound using re-crystallization rather than typical methods of using column chromatography. In addition, the method of the present invention can be usefully used for industrial mass production because sodium borohydride or lithium aluminum hydride with low risk of a fire is used rather than typical methods of using lithium borohydride which is not industrially applicable due to high risk of a fire.

BEST MODE

Hereinafter, the present invention will be described in more detail.

The present invention, as shown in the following Reaction Formula 1, provides a method for preparing a tricyclic derivative of Chemical Formula 1, the method including:

(Step a) preparing a coupling compound of Chemical Formula 6 by amidating a compound of Chemical Formula 5 and a compound of Chemical Formula 2;

(Step b) introducing a sulfonyl group (—SO₂R) by substituting a compound of Chemical Formula 6 prepared during Step a with sulfonyl halide (RSO₂Y) compound under a basic condition; and (Step c) introducing a nitro group by substituting a compound of Chemical Formula 7 prepared during Step b:

[Reaction Formula 1]

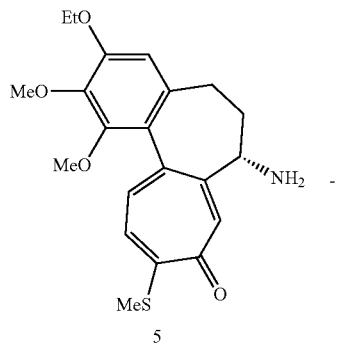

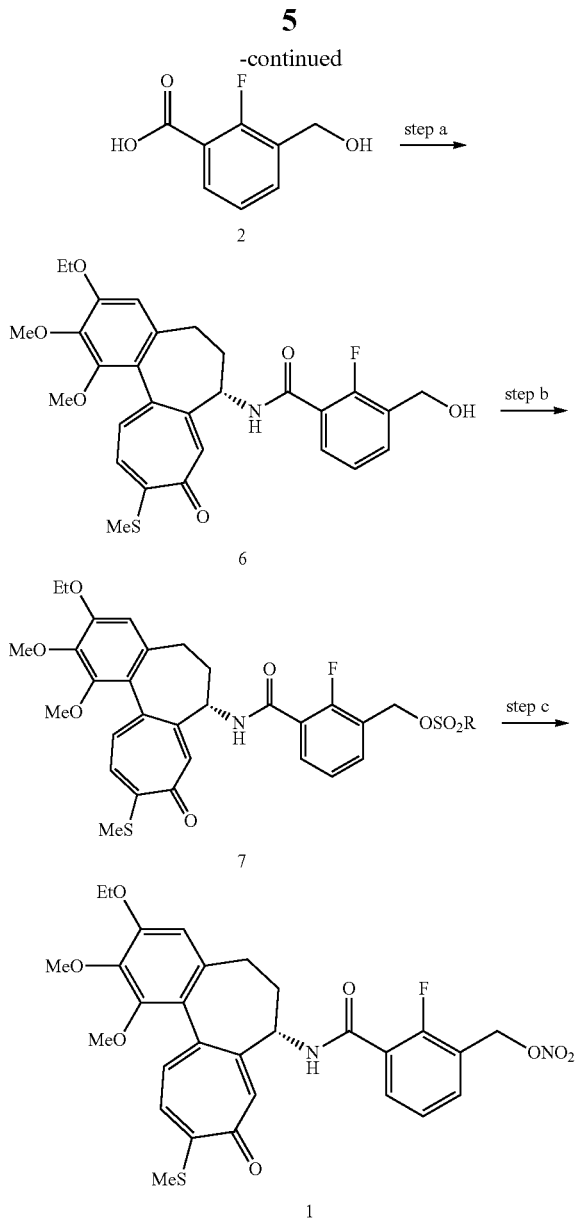

Hereinafter, the preparing method according to the present invention will be more specifically described for each step.

Firstly, the Step a is to prepare a coupling compound of Chemical Formula 6 by amidating a compound of Chemical Formula 5 and a compound of Chemical Formula 2.

The amidation may be performed under presence of a coupling agent such as 1-(3-dimethylaminopropyl)-3-ethyl-carbodiimide (EDCI), 1-hydroxybenzotriazol hydrate (HOBT), and 1,3-dicyclohexyl carbodiimide (DCC). The reaction may be performed without using a base, but generally performed by using a solvent not adversely affecting the amidation, for example, dichloromethane, chloroform, tetrahydrofuran, diethylether, toluene, dimethylformamide, and the like, under presence of a base which may be used for amidation, for example, pyridine, triethylamine, diethylisopropylamine, N-methylmorpholine, and the like. The reaction may be generally performed at a low temperature to high temperature, but not specifically limited thereto. Preferably, the reaction is performed at a room temperature.

Next, the Step b is to introduce sulfonyl group (—SO$_2$R) by substituting a compound of Chemical Formula 6 prepared during the Step a with sulfonyl halide (RSO$_2$Y) compound under a basic condition.

The substitution may introduce sulfonyl group (—SO$_2$R) by dissolving the compound of Chemical Formula 6 using tertiary amine, such as triethylamine, tributylamine, diisobutylethylamine, pyridine, and the like, as a base, and then reacting the resultant solution with sulfonyl halide (RSO$_2$Y) compound. At this point, R of the sulfonyl halide (RSO$_2$Y) compound is unsubstituted or halogen-substituted C1-C4 alkyl, or unsubstituted or C1-C4 alkyl-substituted phenyl, and Y of the sulfonyl halide (RSO2Y) compound is fluoro or chlorine. The preferable example of the sulfonyl halide (RSO$_2$Y) compound may include methanesulfonylchloride, p-toluenesulfonylchloride, trifluoromethansulfonylchloride, and the like. Methanesulfonyl group, p-toluenesulfonyl group, trifluoromethansulfonyl group, and the like may be introduced through the substitution reaction. Dichloromethane, chloroform, tetrahydrofuran, diethylether, and the like may be used as a solvent. The reaction may be generally performed at a low temperature to high temperature, but not specifically limited thereto. Preferably, the reaction may be performed at a low temperature or room temperature.

Next, the Step c is to introduce a nitro group by substituting the compound of Chemical Formula 7 prepared during the Step b.

The substitution may be performed under presence of a solvent not adversely affecting the reaction, for example, chloroform, aqueous solution of acetonitile, dichloromethane, or the like, by using silver nitrate (AgNO$_3$), t-butylammonium nitrate (Bu$_4$NNO$_3$), and the like. The reaction may be generally performed at a low temperature to high temperature, but not specifically limited thereto. Preferably, the reaction may be performed in the temperature range of 40° C. to 60° C.

The preparing method may further include purifying the compounds prepared during the respective steps through re-crystallization. The preparing method according to the present invention enables the yield and purity of the compound as well as the productivity and economical feasibility to be enhanced by purifying a compound through re-crystallization, which differs from typical methods of column chromatography using silica gel. At this point, it is preferable that the re-crystallization temperature be in the range of 0° C. to 25° C. A solvent used for the re-crystallization in each step is as follows.

The Step b may use a compound obtained by purifying the compound of Chemical Formula 6, which is prepared during the Step a, through re-crystallization. For re-crystallization, methanol, toluene, ethylacetate, acetonitrile, or a mixture thereof may be used as a re-crystallization solvent, and a solvent mixture of acetonitrile and ethylacetate may be preferably used.

In addition, the Step c may use a compound obtained by purifying the compound of Chemical Formula 7, which is prepared during the Step b, through re-crystallization. For re-crystallization, acetonitrile, ethylacetate, toluene, and the like may be used as a re-crystallization solvent, and acetonitrile may be preferably used.

Also, the compound of Chemical Formula 1 prepared during the Step c may be purified with the re-crystallization. For re-crystallization, a solvent mixture of methanol and ethanol may be used as a re-crystallization solvent.

Furthermore, the present invention, as shown in the following Reaction Formula 2, provides a method for preparing a compound of Chemical Formula 2, the method including:

(Step 1) esterifying a 2-fluoroisophthalic acid compound of Chemical Formula 8 and alcohol;

(Step 2) preparing a compound of Chemical Formula 10 by hydrolyzing a compound of Chemical Formula 9 prepared during the Step 1;

(Step 3) preparing a compound of Chemical Formula 3 by amidating the compound of Chemical Formula 10 prepared during the Step 2 with an amine compound;

(Step 4) preparing a compound of Chemical Formula 4 by reducing the compound of Chemical Formula 3 prepared during the Step 3; and (Step 5) hydrolyzing the compound of Chemical Formula 4 prepared during the Step 4:

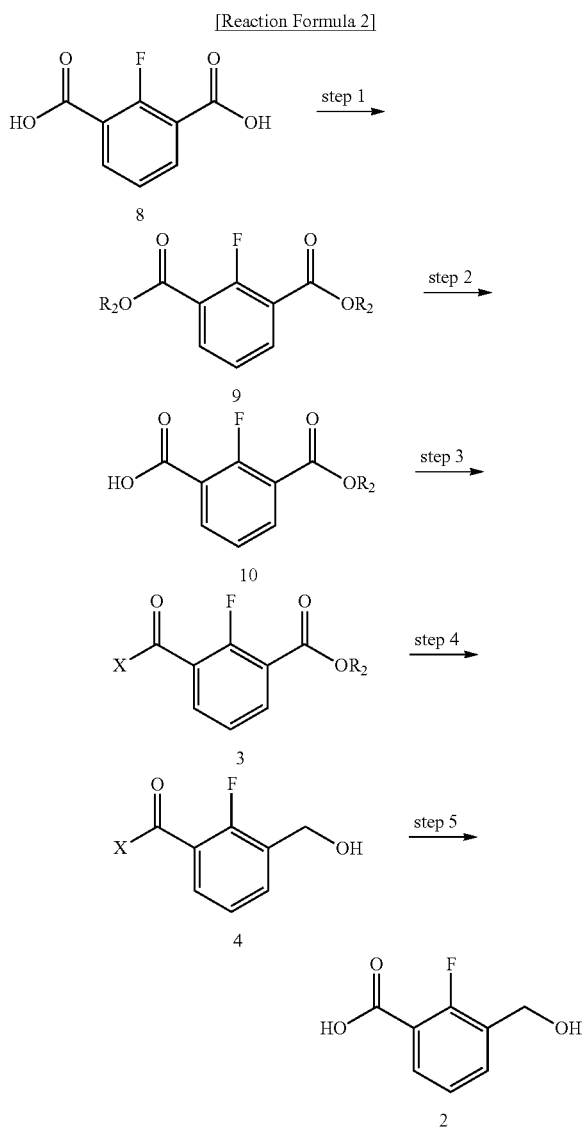

[Reaction Formula 2]

(where, $R_2$ is C1-C8 straight or branched chain alkyl, and X is C4-C6 cycloamino group, or mono- or di-alkylamino group substituted with C1-C4 straight or branched chain alkyl).

Hereinafter, the preparing method according to the present invention will be described in more detail.

Firstly, the Step 1 is to esterify 2-fluoroisophthalic acid compound of Chemical Formula 8 and alcohol.

The esterification may be performed by reacting a compound with alcohol under presence of an acid catalyst. In addition, C1-C8 straight or branched chain alcohol may be preferably used as the alcohol, and more preferably, methanol, ethanol, propanol, buthanol, and the like may be used.

Next, the Step 2 is to prepare a compound of Chemical Formula 10 by hydrolyzing the compound of Chemical Formula 9 prepared during the Step 1.

The hydrolysis may be performed by dissolving the compound of Chemical Formula 9 in a solvent, and reacting the resultant solution with a base. The solvent may include methanol, ethanol, acetone, and the like, and methanol may be preferable used. The base may include sodium hydroxide, potassium hydroxide, and the like, and potassium hydroxide may be preferably used. The reaction may be generally performed at a low temperature to high temperature, but not specifically limited thereto. It is preferable that the reaction is performed at a room temperature for 30 to 50 hours.

The prior art technique for preparing the compound of Chemical Formula 10 (J. Amer. Chem. Soc., 65, 2308) can prepare the compound of Chemical Formula 10 with the yield of 40 to 47% by hydrolyzing with lithium hydroxide or mono-esterifying the compound of Chemical Formula 8; however, the preparing method according to the present invention can prepare the compound of Chemical Formula 10 with high yield, i.e., 75%.

Next, the Step 3 is to prepare the compound of Chemical Formula 3 by amidating the compound of Chemical Formula 10 prepared during the Step 2 with an amine compound.

A coupling method for forming amide bonds by reacting the acid compound of Chemical Formula 10 with an amine compound may include an acid-halide method, an active-ester method, a mixed anhydride method, and the like, and the mixed anhydride method may be preferably used. In the case of using the mixed anhydride method, yield can be increased while suppressing a side reaction to the minimum. The amine compound may preferably be C4-C6 cycloamine or mono- or di-alkylamine substituted with C1-C4 straight or branched chain alkyl. The cycloamine may be more preferably piperidine or pyrrolidine, and the alkyl amine may be more preferably dimethyl amine or diethyl amine.

The amidation may be performed without a base, but generally may be performed under presence of a base which can be used for amidation, for example, pyridine, triethylamine, diethylisopropylamine, N-methylmorpholine, and the like, by using a solvent not adversely affecting the amidation, for example, dichloromethane, chloroform, tetrahydrofuran, diethylether, toluene, dimethylformamide, and the like. The reaction may be generally performed at a low temperature to high temperature, but not limited thereto. Preferably, the reaction may be performed at a room temperature.

Next, the Step 4 is to prepare a compound of Chemical Formula 4 by reducing the compound of Chemical Formula 3 prepared during the Step 3.

The reduction may be performed by dissolving the compound of Chemical Formula 3 in a solvent, dropping a reducing agent, and refluxing and stirring the resultant solution for 1 to 3 hours.

The reducing agent may be sodium borohydride ($NaBH_4$) or lithium aluminumhydride ($LiAlH_4$), and sodium borohydride ($NaBH_4$) may be preferably used.

According to a conventional method for preparing an intermediate compound of Chemical Formula 2 disclosed in Korean Patent Registration No. 0667464, lithium borohydride ($LiBH_4$) is used as a reducing agent in order to reduce ester group, but the lithium borohydride ($LiBH_4$) violently reacts with water to cause harmful gas and flammable gas to be generated, and also has a risk of ignition. Thus, the conventional method is not suitable to be applied to industrial production. Moreover, even in the case of using sodium borohydride (NaBH$_4$) or lithium aluminum hydride (LiAlH$_4$) that are more easily handled as a reducing agent, there is also a disadvantage that selectivity is decreased to thereby reduce all of two ester groups of the compound of Chemical Formula 6. However, since the preparing method according to the present invention uses sodium borohydride (NaBH$_4$) or lithium aluminumhydride (LiAlH$_4$) that have a low risk of a fire or explosion when compared to lithium borohydride, the inventive method can be suitably applied to industrial mass production and improve the yield as well. In addition, the inventive method can also overcome the disadvantage of low selectivity caused by using the above-described reducing agent because amide bonds are formed by amidating the compound of Chemical Formula 10 and piperidine in the Step 3.

Next, the Step 5 is to hydrolyze the compound of Chemical Formula 4 prepared during the Step 4. The hydrolysis may be performed by refluxing and stirring for 30 to 50 hours under presence of a base. Sodium hydroxide, potassium hydroxide, lithium hydroxide, and the like may be used as the base.

Also, the present invention provides a compound of following Chemical Formula 3 that is an intermediate produced during the preparing of the compound of Chemical Formula 2:

[Chemical Formula 3]

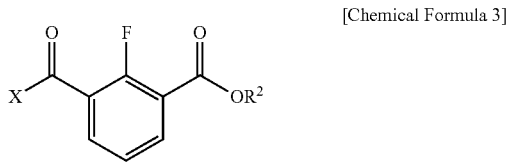

wherein,
R$^2$ is C1-C8 straight or branched chain alkyl; and
X is C4-C6 cycloamino group, or mono- or di-alkylamino group substituted with C1-C4 straight or branched chain alkyl,
Preferably,
R$^2$ is methyl, ethyl, propyl, or butyl,
X is piperidyl group, pyrrolidinyl group, dimethylamino group, or diethylamino group.

The present invention also provides a compound of following Chemical Formula 4 which is an intermediate produced during the preparing of the compound of Chemical Formula 2:

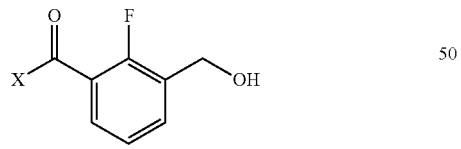

(where,
X is as defined in Chemical Formula 3).

Also, the present invention, as shown in the following Reaction Formula 3, provides a method for preparing a tricyclic derivative of Chemical Formula 1, the method including:

(Step A) esterifying a 2-fluoroisophthalic acid compound of Chemical Formula 8 and alcohol;
(Step B) preparing a compound of Chemical Formula 10 by hydrolyzing the compound of Chemical Formula 9 prepared during the Step A;
(Step C) preparing a compound of Chemical Formula 3 by amidating the compound of Chemical Formula 10 prepared during the Step B with an amine compound;

(Step D) preparing a compound of Chemical Formula 4 by reducing the compound of Chemical Formula 3 prepared during the Step C;
(Step E) hydrolyzing the compound of Chemical Formula 4 prepared during the Step D;
(Step F) preparing a coupling compound of Chemical Formula 6 by amidating the compound of Chemical Formula 5 and the compound of Chemical Formula 2 prepared during the Step E;
(Step G) introducing a sulfonyl group (—SO$_2$R) by substituting the compound of Chemical Formula 6 prepared during the Step F under a basic condition; and
(Step H) introducing a nitro group by substituting the compound of Chemical Formula 7 prepared during the Step G:

[Reaction Formula 3]

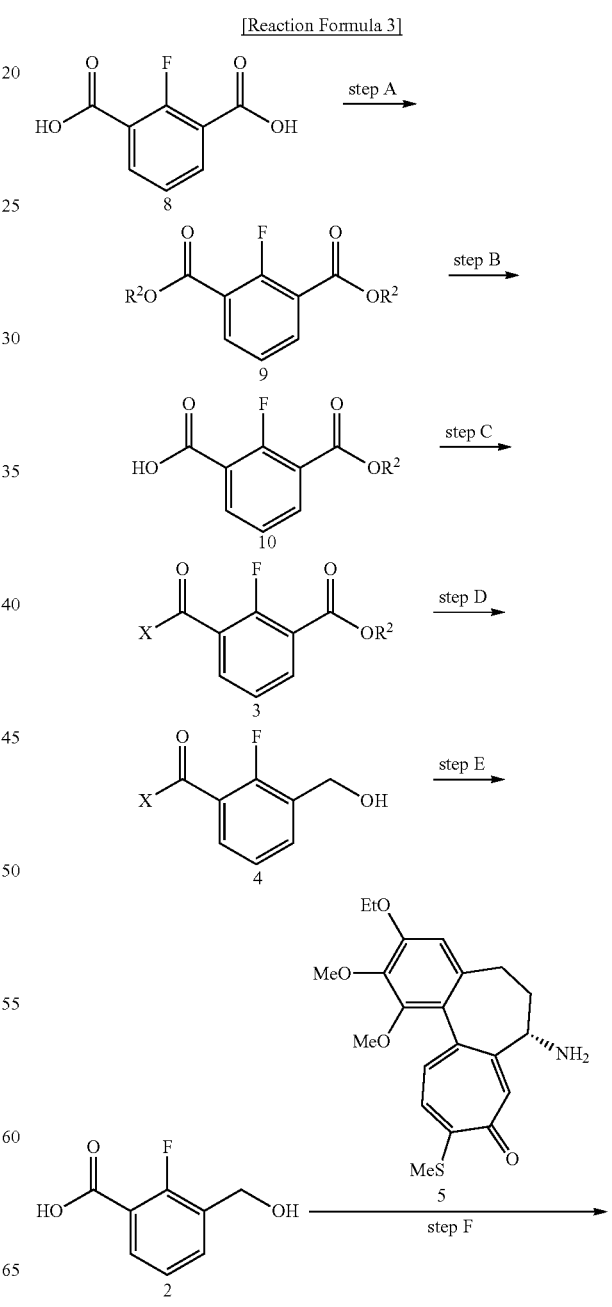

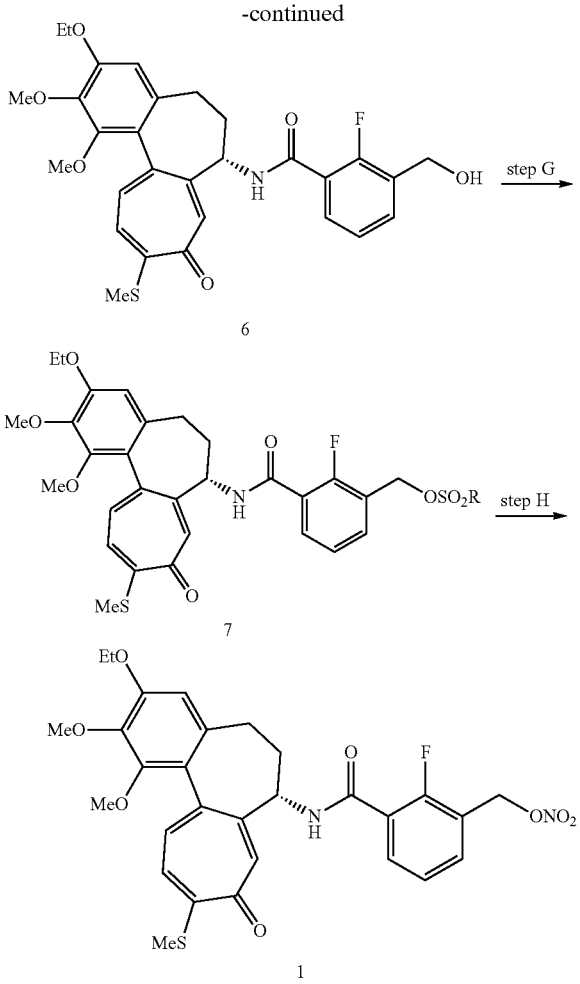

(where,

R² is C1-C8 straight or branched chain alkyl;

X is C4-C6 cycloamino group, or mono- or di-alkylamino group substituted with C1-C4 straight or branched chain alkyl; and R is unsubstituted or halogen-substituted C1-C4 alkyl, or unsubstituted or C1-C4 alkyl-substituted phenyl.

The Step A to Step E may be performed with the same method as Step 1 to Step 5 of Reaction Formula 1, and the Step F to Step H may be performed with the same method as Step a to Step c of Reaction Formula 2.

MODE FOR INVENTION

Hereinafter, the present invention will be described in more detail.

The following Examples are merely provided for illustrating the present invention, but details of the present invention will be not limited to the following Examples.

Example 1

Preparation of 2-fluoro-3-(hydroxymethyl)benzoic acid

Step 1: Preparation of dimethyl-2-fluoroisophthalate 430 g (2.34 mol) of 2-fluoroisophthalic acid was dissolved in 4.3 l of methanol; sulfuric acid with catalytic amount was dropped; and then the resultant solution was refluxed and stirred. 860 ml of a saturated sodium bicarbonate aqueous solution was added to the finished reaction mixture, and then distilled under reduced pressure with methanol. 860 ml of distilled water was added and then stirred for 1 hour at a room temperature. A resulting solid was filtered, washed with water, and then dried to obtain 471 g of dimethyl-2-fluoroisophthalate in a white solid phase.

Yield: 95.0%

1H NMR (400 MHz, DMSO-$d_6$): δ 8.10-8.06 (m, 2H), 7.43 (t, 1H, J=8.0 Hz), 3.86 (s, 6H)

Step 2: Preparation of 2-fluoro-3-(methoxycarbonyl)benzoic acid 471 g (2.22 mol, 1.0 eq) of dimethyl-2-fluoroisophthalate obtained from the Step 1 was dissolved in 4 l of methanol, and then 143 g (2.55 mol, 1.15 eq) of potassium hydroxide that was dissolved in 1 l of methanol was dropped thereto at a room temperature. The reaction mixture was stirred for 40 hours at a room temperature. After completing the reaction, methanol was distilled under reduced pressure, 2.5 l of distilled water was added, and then the resultant mixture was washed with 1.0 l of ethylacetate. A obtained aqueous layer was cooled to 0° C., and then 318 ml of hydrochloric acid was slowly added. It was stirred for 2 hours at 0° C.; produced crystals were filtered; washed with water; and then dried to obtain 330 g of 2-fluoro-3-(methoxycarbonyl)benzoic acid in a white solid phase.

Yield: 75.0%

1H NMR (400 MHz, DMSO-$d_6$): δ 8.10-8.04 (m, 2H), 7.41 (t, 1H, J=8.0 Hz), 3.87 (s, 3H)

Step 3: Preparation of methyl 2-fluoro-3-(piperidine-1-carbonyl)benzoate 162 g (1.47 mol, 1.05 eq) of N-methylmorphorine was added to the mixed solution of 278 g (1.4 mol, 1.0 eq) of 2-fluoro-3-(methoxycarbonyl)benzoic acid obtained from the Step 2 and 2.7 l of dichloromethane, and then stirred for 30 minutes at 0° C. 191 ml (1.47 mol, 1.05 eq) of isobutyl chloromate was slowly added, and then stirred for 1 hour at 0° C. 139 ml (1.4 mol, 1.0 eq) of piperidine was slowly added, and then stirred for 1 hour at a room temperature. After completing the reaction, the reaction solution was washed with 560 ml of a saturated sodium bicarbonate aqueous solution, 560 ml of a saturated ammonium chloride aqueous solution, and 1 l of distilled water in order. A obtained organic layer was dehydrated with magnesium sulfate anhydrous, filtered, and then concentrated under reduced pressure to obtain 371 g of methyl 2-fluoro-3-(piperidine-1-carbonyl) benzoate in a red-yellow oil phase Yield: 99%

1H NMR (400 MHz, DMSO-$d_6$): δ 7.92 (td, 1H, J=7.6 Hz, J=1.6 Hz), 7.64-7.60 (m, 1H), 7.38 (t, 1H, J=7.6 Hz), 3.85 (s, 3H), 3.60 (br, 2H), 3.14 (br, 2H), 1.16-1.40 (m, 6H)

Step 4: Preparation of (2-fluoro-3-(hydroxymethylphenyl)(piperidine-1-yl)methanone 1.73 g (6.52 mmol, 1.0 eq) of 2-fluoro-3-(piperidine-1-carbonyl)benzoate obtained from the Step 3 was dissolved in 17 ml of tetrahydrofuran, and then 987 mg (26.1 mmol, 4.0 eq) of sodium borohydride that was dissolved in 4.3 ml of distilled water was dropped. The reaction mixture was refluxed and stirred for 2 hours. The reaction solution was cooled to a room temperature, then hydrochloric acid was added to acidify the solution (pH ~2.0), and then the solution was extracted with dichloromethane. An organic layer was washed with a diluted sodium bicarbonate aqueous solution, dehydrated with magnesium sulfate anhydrous; and then concentrated under reduced pressure. 8 ml of ethylacetate was added to the obtained compound in a white solid phase, and then refluxed and stirred for 30 minutes. After cooling to a room temperature, the resulting solid was filtered and then dried to obtain 1.33 g of (2-fluoro-3-(hydroxymethyl-phenyl) (piperidine-1-yl)methanone.
Yield: 94.4%
1H NMR (400 MHz, DMSO-$d_6$): δ 7.56-7.50 (m, 1H), 7.27-7.22 (m, 2H), 5.36 (t, 1H, J=6.0 Hz), 4.56 (d, 2H, J=6.0 Hz), 3.60 (br, 2H), 3.17-3.15 (m, 2H), 1.60-1.39 (m, 6H)

Step 5: Preparation of
2-fluoro-3-(hydroxymethyl)benzoic acid 37.1 g (0.927 mol, 5.0 eq) of sodium hydroxide was added to the mixture of 44.0 g (0.185 mol) of (2-fluoro-3-(hydroxymethyl-phenyl) (piperidine-1-yl)methanone and 220 ml of distilled water, and then refluxed and stirred for 40 hours. After completing the reaction, the reaction mixture was cooled to a room temperature. An aqueous layer was washed with dichloromethane; cooled to 0° C.; and then hydrochloric acid was added to acidify (pH=2.0). It was extracted with ethylacetate; the obtained organic layer was dehydrated with magnesium sulfate anhydrous; filtered; and then concentrated to obtain 29.5 g of 2-fluoro-3-(hydroxymethyl)benzoic acid in a white solid phase.
Yield: 93.6%
1H NMR (400 MHz, DMSO-$d_6$): δ 7.74 (t, 1H, J=3.2 Hz), 7.68 (t, 1H, J=3.2 Hz), 7.27 (t, 1H, J=3.2 Hz), 4.57 (s, 2H)

Example 2

Preparation of N-3-ethoxy-1,2-dimethoxy-10-methylsulfanyl-9-oxo-5,6,7,9-tetrahydro-benzo[a]heptalene-7-yl)-2-fluoro-3-nitrooxymethylbenzamide Step a: Preparation of N-3-ethoxy-1,2-dimethoxy-10-methylsulfanyl-9-oxo-5,6,7,9-tetrahydro-benzo[a]heptalene-7-yl)-2-fluoro-3-hydroxymethylbenzamide 163 g (421 mmol, 1.0 eq) of (7S)-7-amino-3-ethoxy-1,2,-dimethoxy-10-methylsulfanyl-6,7-dihydro-5H-benzo[a] heptalene-9-one was dissolved in 1.4 l of dichloromethane, and then 105 g (547 mmol, 1.3 eq) of 1-(3-dimethylaminopropyl)-3-ethylcarbodiimide and 5.7 g (42.1 mmol, 0.1 eq) of 1-hydroxybenzotriazol hydrate were added. 93.6 g (54 7 mmol, 1.3 eq) of 2-fluoro-3-(hydroxymethyl)benzoic acid was added and then stirred for 2 hours at a room temperature. After completing the reaction, the reaction mixture was washed with purified water; dehydrated with magnesium sulfate anhydrous; and then concentrated under reduced pressure to obtain a product in a yellow solid phase. The mixed solution of 300 ml of acetonitrile and 250 ml of ethyl acetate was added to the obtained product, and then stirred for 30 minutes at a room temperature and for 2 hours at 0° C. The resulting solid was filtered, washed with ethyl acetate, and then dried to obtain 211 g of N-(3-ethoxy-1,2-dimethoxy-10-methylsulfanyl-9-oxo-5,6,7,9-tetrahydro-benzo[a]heptalene-7-yl)-2-fluoro-3-hydroxymethylbenzamide in a yellow solid phase.
Yield: 92.9%
Purity (by HPLC): 98.4%
1H NMR (400 MHz, DMSO-$d_6$): δ 9.12 (d, 1H, J=7.6 Hz), 7.58 (t, 1H, J=7.2 Hz), 7.38 (t, 1H, J=7.2 Hz), 7.30-7.17 (m, 4H), 6.80 (s, 1H), 5.41 (t, 1H, J=5.6 Hz), 4.59 (d, 2H, J=5.6 Hz), 4.56-4.50 (m, 1H), 4.17-4.08 (m, 2H), 3.82 (s, 3H), 3.59 (s, 3H), 2.67-2.60 (m, 1H), 2.42 (s, 3H), 2.29-1.97 (m, 3H), 1.38 (t, 3H, J=6.8 Hz).

Step b: Preparation of methanesulfonic acid 3-(3-ethoxy-1,2-dimethoxy-10-methylsulfanyl-9-oxo-5,6,7,9-tetrahydro-benzo[a]heptalene-7-ylcarbamoyl)-2-fluoro-benzyl ester The mixture of 500 ml of dichloromethane and 50 g (92.7 mmol, 1.0 eq) of N-(3-ethoxy-1,2-dimethoxy-10-methylsulfanyl-9-oxo-5,6,7,9-tetrahydro-benzo[a]heptalene-7-yl)-2-fluoro-3-hydroxymethylbenzamide obtained during the Step a in Example 2 was cooled to 0° C., and then 20.6 ml (148 mmol, 1.6 eq) of triethylamine was added to the mixture. 10.7 ml (139 mmol, 1.5 eq) of methanesulfonylchloride was dropped to the reaction mixture, and then stirred for 30 minutes at 0° C. After completing the reaction, the reaction mixture was washed with 300 ml of purified water, dehydrated with magnesium sulfate anhydrous, and then concentrated under reduced pressure to thereby obtain a product in a yellow solid phase. 100 ml of acetonitrile was added to the obtained product, and then stirred for 30 minutes at a room temperature and then for 2 hours at 0° C. The resulting solid was filtered and dried to obtain 51.4 g of 3-(3-ethyoxy-1,2-dimethoxy-10-methylsulfanyl-9-oxo-5,6,7,9-tetrahydro-benzo[a]heptalene-7-ylcarbamoyl)-2-fluoro-benzyl ester in a yellow solid phase.
Yield: 89.8%
Purity (by HPLC): 96.7%
1H NMR (400 MHz, DMSO-$d_6$): δ 9.24 (d, 1H, J=7.2 Hz), 7.68 (t, 1H, J=7.2 Hz), 7.57 (t, 1H, J=7.2 Hz), 7.36-7.16 (m, 4H), 6.81 (s, 1H), 5.35 (s, 2H), 4.56-4.50 (m, 1H), 4.14-4.09 (m, 2H), 3.82 (s, 3H), 3.59 (s, 3H), 3.29 (s, 3H), 2.66-2.61 (m, 1H), 2.42 (s, 3H), 2.30-1.97 (m, 3H), 1.38 (t, 3H, J=6.8 Hz)

Step c: Preparation of N-(3-ethoxy-1,2-dimethoxy-10-methylsulfanyl-9-oxo-5,6,7,9-tetrahydro-benzo[a] heptalene-7-yl)-2-fluoro-3-nitrooxymethylbenzamide 68.8 g (405 mmol, 4.5 eq) of silver nitrate was added to the mixture of 500 ml of acetonitrile and 55.6 g (90.1 mmol, 1.0 eq) of 3-(3-ethyoxy-1,2-dimethoxy-10-methylsulfanyl-9-oxo-5,6,7,9-tetrahydro-benzo[a]heptalene-7-ylcarbamoyl)-2-fluoro-benzyl ester obtained from the Step b of Example 2, and then stirred for 18 hours at 50° C. After completing the reaction, purified water was added and then the mixture was extracted with dichloromethane. An organic layer was dehydrated with magnesium sulfate anhydrous, filtered on a silica gel pad, and then concentrated under reduced pressure to obtain a product. Methanol and ethanol were added to the obtained product, and then stirred for 30 minutes at a room temperature and then for 1 hour at 0° C. The resulting solid was filtered and then dried to obtain 38.8 g of N-(3-ethoxy-1,2-dimethoxy-10-methylsulfanyl-9-oxo-5,6,7,9-tetrahydro-benzo[a]heptalene-7-yl)-2-fluoro-3-nitrooxymethylbenzamide in a yellow solid phase.
Yield: 73.7%
Purity (by HPLC): 99.8%
1H NMR (400 MHz, DMSO-$d_6$): δ 9.24 (d, 1H, J=6.0 Hz), 7.71-7.56 (m, 2H), 7.36-7.16 (m, 4H), 6.81 (s, 1H), 5.69 (s, 2H), 4.56-4.50 (m, 1H), 4.15-4.09 (m, 2H), 3.82 (s, 3H), 3.59 (s, 3H), 2.66-2.61 (m, 1H), 2.42 (s, 3H), 2.28-1.97 (m, 3H), 1.38 (t, 3H, J=6.8 Hz)

INDUSTRIAL APPLICABILITY

The present invention, which relates to a method for preparing an intermediate of tricyclic derivative with high yield and purity, and to a method for preparing a tricyclic derivative using the intermediate, can provide tricyclic derivative with high purity and yield as well as high productivity and economic feasibility as compared with typical methods, and also can be usefully used for industrial mass production. Thus, the present invention is industrially applicable.

What we claimed is:

1. A method for preparing a tricyclic derivative of Chemical Formula 1, as shown in following Reaction Formula 1, the method comprising:

(Step a) preparing a coupling compound of Chemical Formula 6 by amidating a compound of Chemical Formula 5 and a compound of Chemical Formula 2;

(Step b) introducing a sulfonyl group (—SO$_2$R) by substituting the compound of Chemical Formula 6 prepared during the Step a with sulfonyl halide (RSO$_2$Y) compound under a basic condition; and (Step c) introducing a nitro group by substituting the compound of Chemical Formula 7 prepared during the Step b:

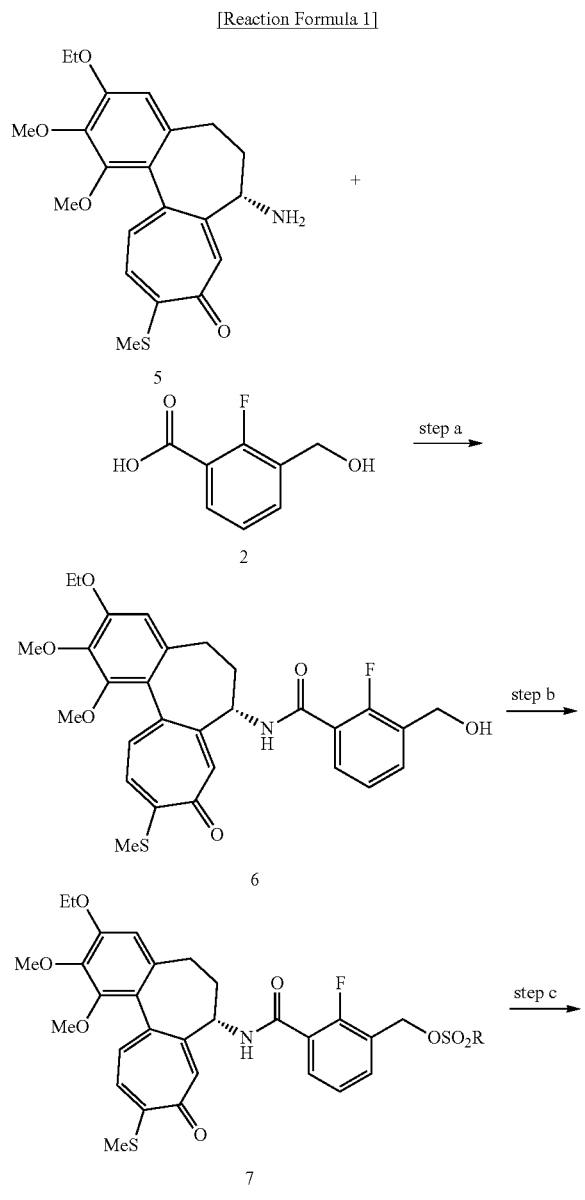

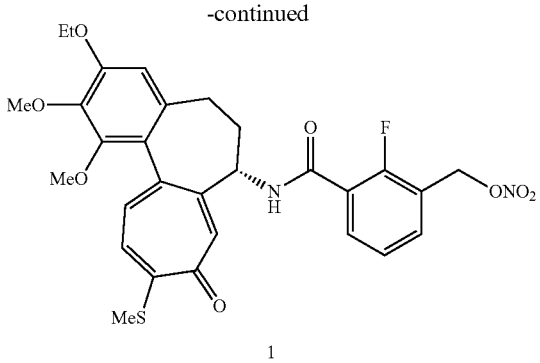

(where,

R is unsubstituted or halogen-substituted C1-C4 alkyl, or unsubstituted or C1-C4 alkyl-substituted phenyl; and Y is fluoro or chloro).

2. The method according to claim 1, wherein the sulfonyl halide (RSO$_2$Y) compound is one selected from the group consisting of methanesulfonylchloride, p-toluenesulfonylchloride, and trifluoromethanesulfonylchloride.

3. The method according to claim 1, wherein the Step b uses a compound obtained by purifying the compound of Chemical Formula 6 prepared during the Step a, through re-crystallization.

4. The method according to claim 3, wherein the re-crystallization uses one selected from the group consisting of methanol, toluene, ethylacetate, acetonitrile, or a solvent mixture thereof as a re-crystallization solvent.

5. The method according to claim 1, wherein the Step c uses a compound obtained by purifying the compound of Chemical Formula 7 prepared during the Step b, through re-crystallization.

6. The method according to claim 5, wherein the re-crystallization uses one selected from the group consisting of acetonitrile, ethylacetate, and toluene as a re-crystallization solvent.

7. The method according to claim 1, wherein the compound of Chemical Formula 1 prepared by performing the Step c is purified through re-crystallization.

8. The method according to claim 7, wherein the re-crystallization uses a solvent mixture of methanol and ethanol as a re-crystallization solvent.

9. A method for preparing a compound of Chemical Formula 2, as shown in the following Reaction Formula 2, the method comprising:

(Step 1) esterifying a 2-fluoroisophthalic acid compound of Chemical Formula 8 and alcohol;

(Step 2) preparing a compound of Chemical Formula 10 by hydrolyzing the compound of Chemical Formula 9 prepared during the Step 1;

(Step 3) preparing a compound of Chemical Formula 3 by amidating the compound of Chemical Formula 10 prepared during the Step 2 with an amine compound;

(Step 4) preparing a compound of Chemical Formula 4 by reducing the compound of Chemical Formula 3 prepared during the Step 3; and (Step 5) hydrolyzing the compound of Chemical Formula 4 prepared during the Step 4:

[Reaction Formula 2]

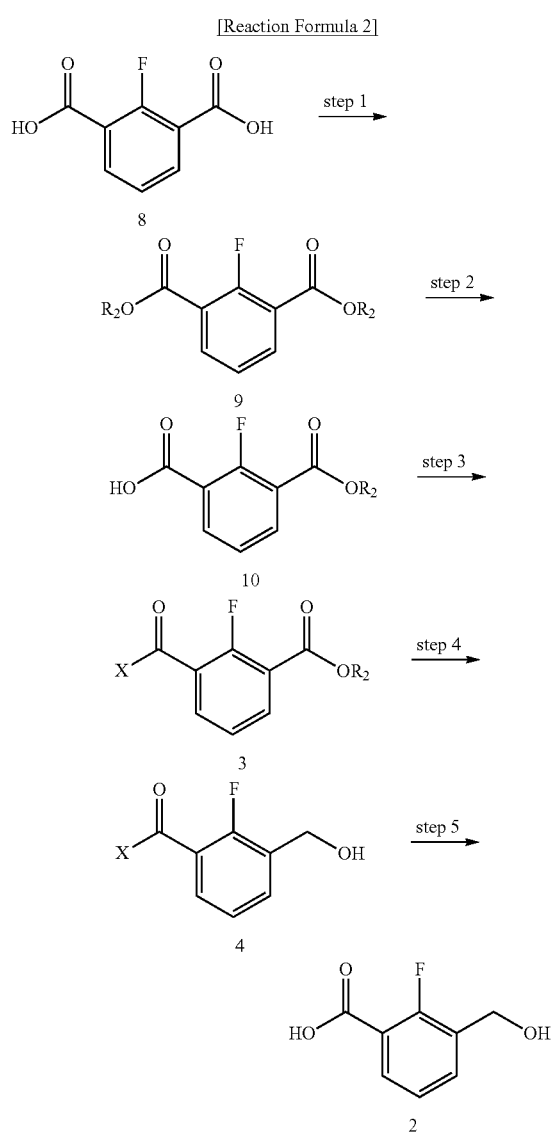

(where, $R_2$ is C1-C8 straight or branched chain alkyl, and X is C4-C6 cycloamino group, or mono- or di-alkylamino group substituted with C1-C4 straight or branched chain alkyl).

10. The method according to claim 9, wherein the alcohol of the Step 1 is C1-C8 straight or branched chain alcohol.

11. The method according to claim 9, wherein the amidation of the Step 3 uses a mixed anhydride method.

12. The method according to claim 9, wherein the amine compound of the Step 3 is C4-C6 cycloamine, or mono- or di-alkylamine substituted with C1-C4 straight or branched chain alkyl.

13. The method according to claim 12, wherein the cycloamine is piperidine or pyrrolidine and the alkyl amine is dimethyl amine or diethyl amine.

14. The method according to claim 9, wherein the reduction of the Step 4 uses sodium borohydride ($NaBH_4$) or lithium aluminumhydride ($LiAlH_4$) as a reducing agent.

15. The method according to claim 9, wherein the Step 5 uses a compound obtained by purifying the compound of Chemical Formula 4 prepared during the Step 4, through re-crystallization.

16. The method according to claim 15, wherein the re-crystallization uses one selected from the group consisting of diethylether, tetrahydrofuran, and ethylacetate as a re-crystallization solvent.

17. A compound of following Chemical Formula 3 which is an intermediate produced in the preparing of the compound of Chemical Formula 2:

[Chemical Formula 3]

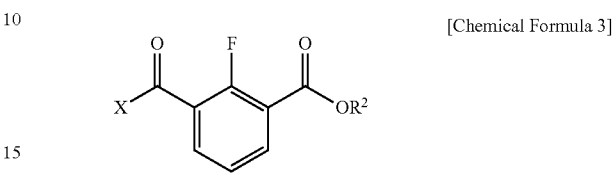

(where,
$R^2$ is C1-C8 straight or branched chain alkyl; and
X is C4-C6 cycloamino group, or mono- or di-alkylamino group substituted with C1-C4 straight or branched chain alkyl).

18. The compound according to claim 17, wherein the $R^2$ is methyl, ethyl, propyl, or butyl; and
X is piperidyl group, pyrrolidyl group, dimethylamino group, or diethylamino group.

19. A compound of following Chemical Formula 4 which is an intermediate produced in the preparing of the compound of Chemical Formula 2:

[Chemical Formula 4]

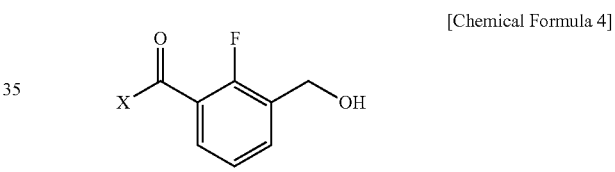

X is as defined in claim 17.

20. A method for preparing a tricyclic derivative of Chemical Formula 1, as shown in the following Reaction Formula 3, the method comprising:
(Step A) esterifying a 2-fluoroisophthalic acid compound of Chemical Formula 8 and alcohol;
(Step B) preparing a compound of Chemical Formula 10 by hydrolyzing the compound of Chemical Formula 9 prepared during the Step A;
(Step C) preparing a compound of Chemical Formula 3 by amidating the compound of Chemical Formula 10 prepared during the Step B with an amine compound;
(Step D) preparing a compound of Chemical Formula 4 by reducing the compound of Chemical Formula 3 prepared during the Step C;
(Step E) hydrolyzing the compound of Chemical Formula 4 prepared during the Step D;
(Step F) preparing a coupling compound of Chemical Formula 6 by amidating the compound of Chemical Formula 5 and the compound of Chemical Formula 2 prepared during the Step E;
(Step G) introducing a sulfonyl group (—$SO_2R$) by substituting the compound of Chemical Formula 6 prepared during the Step F under a basic condition; and
(Step H) introducing a nitro group by substituting the compound of Chemical Formula 7 prepared during the Step G:

[Reaction Formula 3]
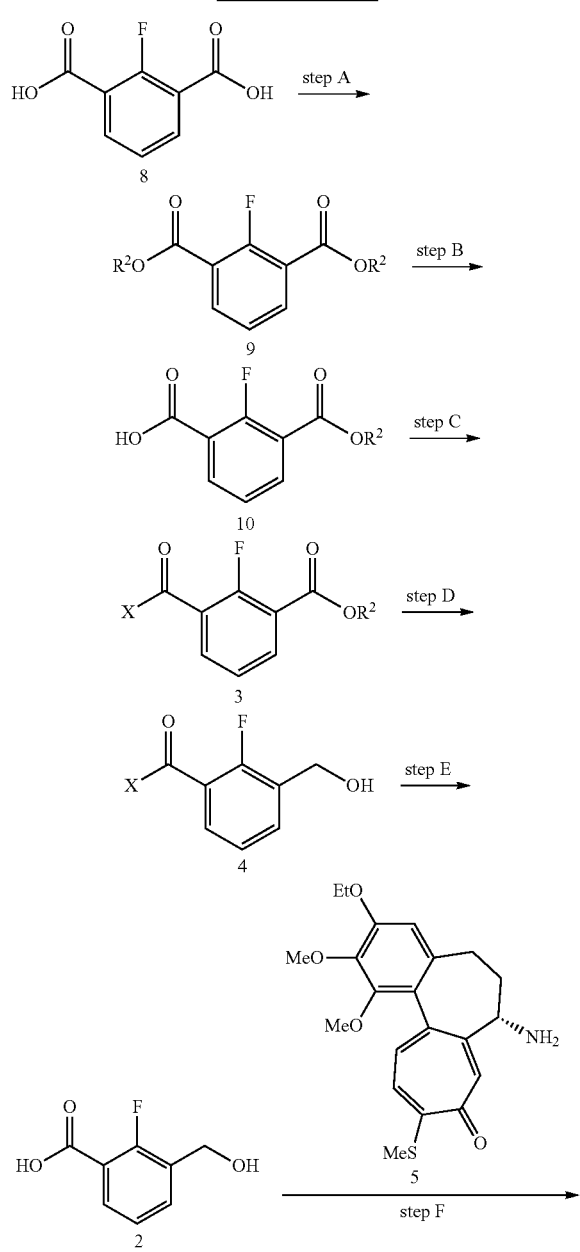
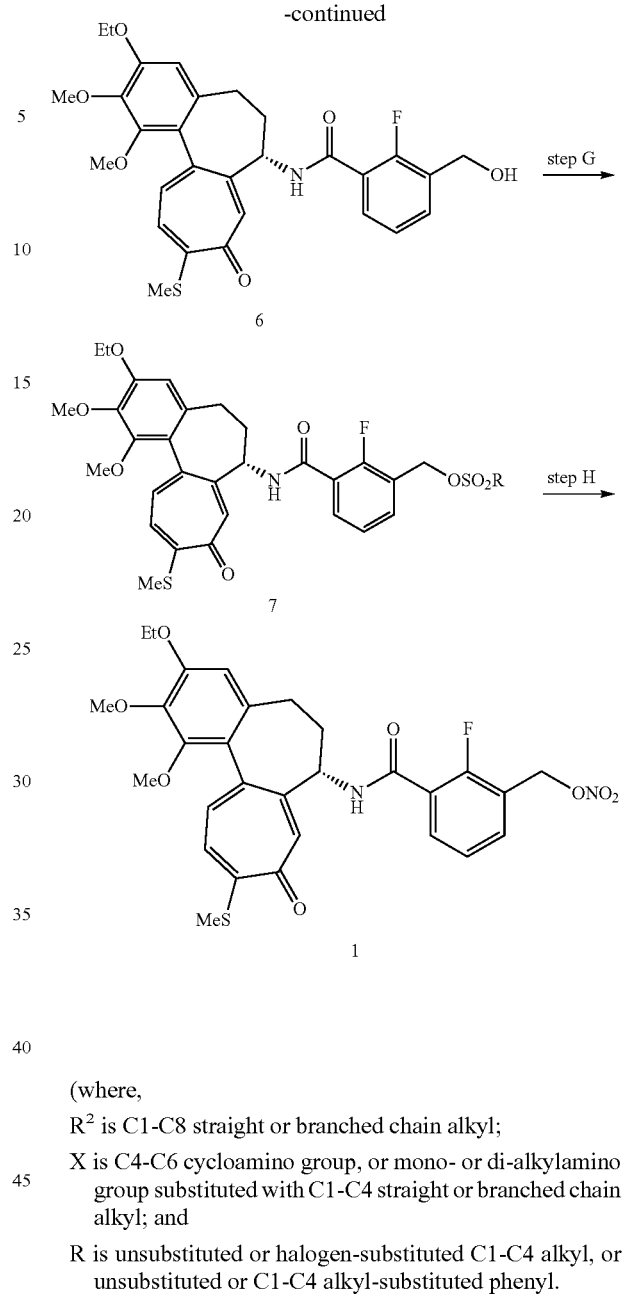
(where,
R² is C1-C8 straight or branched chain alkyl;
X is C4-C6 cycloamino group, or mono- or di-alkylamino group substituted with C1-C4 straight or branched chain alkyl; and
R is unsubstituted or halogen-substituted C1-C4 alkyl, or unsubstituted or C1-C4 alkyl-substituted phenyl.
* * * * *